(12) United States Patent
Taylor et al.

(10) Patent No.: US 11,529,134 B2
(45) Date of Patent: *Dec. 20, 2022

(54) SYNDESMOSIS TREATMENT CONSTRUCT

(71) Applicant: In2Bones USA, LLC, Memphis, TN (US)

(72) Inventors: Alan G. Taylor, Memphis, TN (US); Rebecca Hawkins Wahl, Escondido, CA (US)

(73) Assignee: In2Bones USA, LLC, Memphis, TN (US)

( * ) Notice: Subject to any disclaimer, the term of this patent is extended or adjusted under 35 U.S.C. 154(b) by 555 days.

This patent is subject to a terminal disclaimer.

(21) Appl. No.: 16/717,981

(22) Filed: Dec. 17, 2019

(65) Prior Publication Data

US 2021/0177395 A1 Jun. 17, 2021

(51) Int. Cl.
*A61B 17/04* (2006.01)

(52) U.S. Cl.
CPC ...... *A61B 17/0401* (2013.01); *A61B 17/0485* (2013.01); *A61B 2017/0459* (2013.01); *A61B 2017/0496* (2013.01)

(58) Field of Classification Search
CPC ............ A61B 17/0401; A61B 17/0485; A61B 17/0459; A61B 17/0496
See application file for complete search history.

(56) References Cited

U.S. PATENT DOCUMENTS

| | | | | |
|---|---|---|---|---|
| 5,921,986 A * | 7/1999 | Bonutti | ............... | A61B 17/0401 606/57 |
| 6,099,568 A * | 8/2000 | Simonian | ............... | A61F 2/0811 623/13.11 |
| 6,110,207 A * | 8/2000 | Eichhorn | ............... | A61F 2/0811 606/232 |
| 6,460,379 B2 | 10/2002 | Pawlenko et al. | | |
| 8,162,997 B2 * | 4/2012 | Struhl | ................... | A61F 2/0811 606/232 |
| 9,179,950 B2 | 11/2015 | Zajec et al. | | |
| 10,206,670 B2 * | 2/2019 | Thornes | ............. | A61B 17/0401 |
| 10,758,224 B2 * | 9/2020 | Medoff | ............. | A61B 17/0401 |

(Continued)

FOREIGN PATENT DOCUMENTS

WO  WO-2017/210659  12/2017

OTHER PUBLICATIONS

PCT International Search Report, dated Mar. 17, 2021.

*Primary Examiner* — Phong Son H Dang
(74) *Attorney, Agent, or Firm* — Rutan & Tucker LLP; Hani Z. Sayed

(57) ABSTRACT

An apparatus and method are provided for a syndesmosis treatment construct configured to be placed into a cinched configuration that presses a first bone against a second bone. The syndesmosis treatment construct comprises a proximal fixator to contact the first bone and a distal fixator to contact the second bone. A first suture and a second suture are parallelly looped through the distal fixator. A free splice slidably rides on proximal ends and distal ends of both of the first and second sutures. The distal ends are looped through the proximal fixator and bound within a stitch splice. The proximal ends are passed outside of the stitch splice and through the proximal fixator. The free splices compress and seize the proximal ends during pulling of the proximal ends by a practitioner so as to maintain the cinched configuration.

5 Claims, 6 Drawing Sheets

(56) References Cited

U.S. PATENT DOCUMENTS

| | | | |
|---|---|---|---|
| 10,779,868 B2* | 9/2020 | O'Connor | A61B 17/1615 |
| 2002/0019634 A1* | 2/2002 | Bonutti | A61B 17/82 |
| | | | 606/57 |
| 2003/0236555 A1* | 12/2003 | Thornes | A61B 17/842 |
| | | | 606/232 |
| 2005/0033363 A1* | 2/2005 | Bojarski | A61B 17/06166 |
| | | | 606/228 |
| 2006/0190041 A1* | 8/2006 | Fallin | A61B 17/0487 |
| | | | 606/232 |
| 2007/0083236 A1* | 4/2007 | Sikora | A61B 17/0401 |
| | | | 606/232 |
| 2008/0177302 A1* | 7/2008 | Shurnas | A61B 17/0401 |
| | | | 606/228 |
| 2008/0188935 A1* | 8/2008 | Saylor | A61B 17/0401 |
| | | | 623/13.14 |
| 2008/0195148 A1* | 8/2008 | Cook | A61D 1/00 |
| | | | 606/228 |
| 2008/0208252 A1* | 8/2008 | Holmes | A61B 17/842 |
| | | | 606/232 |
| 2010/0249930 A1* | 9/2010 | Myers | A61B 17/1764 |
| | | | 623/13.14 |
| 2010/0268273 A1* | 10/2010 | Albertorio | A61B 17/0487 |
| | | | 606/232 |
| 2012/0123541 A1* | 5/2012 | Albertorio | A61B 17/0401 |
| | | | 606/232 |
| 2013/0096612 A1 | 4/2013 | Zajac et al. | |
| 2016/0030035 A1* | 2/2016 | Zajac | A61B 17/86 |
| | | | 606/232 |
| 2016/0051250 A1* | 2/2016 | Thornes | A61B 17/68 |
| | | | 606/232 |
| 2016/0144066 A1 | 5/2016 | Long et al. | |
| 2017/0209140 A1* | 7/2017 | Thornes | A61B 17/68 |
| 2018/0221010 A1 | 8/2018 | Lund | |
| 2019/0365375 A1* | 12/2019 | Thornes | A61B 17/0401 |
| 2020/0196997 A1* | 6/2020 | Thornes | A61B 17/68 |
| 2021/0378654 A1* | 12/2021 | Lombardo | A61B 17/06066 |
| 2022/0240918 A1* | 8/2022 | Qi | A61B 17/06166 |

* cited by examiner

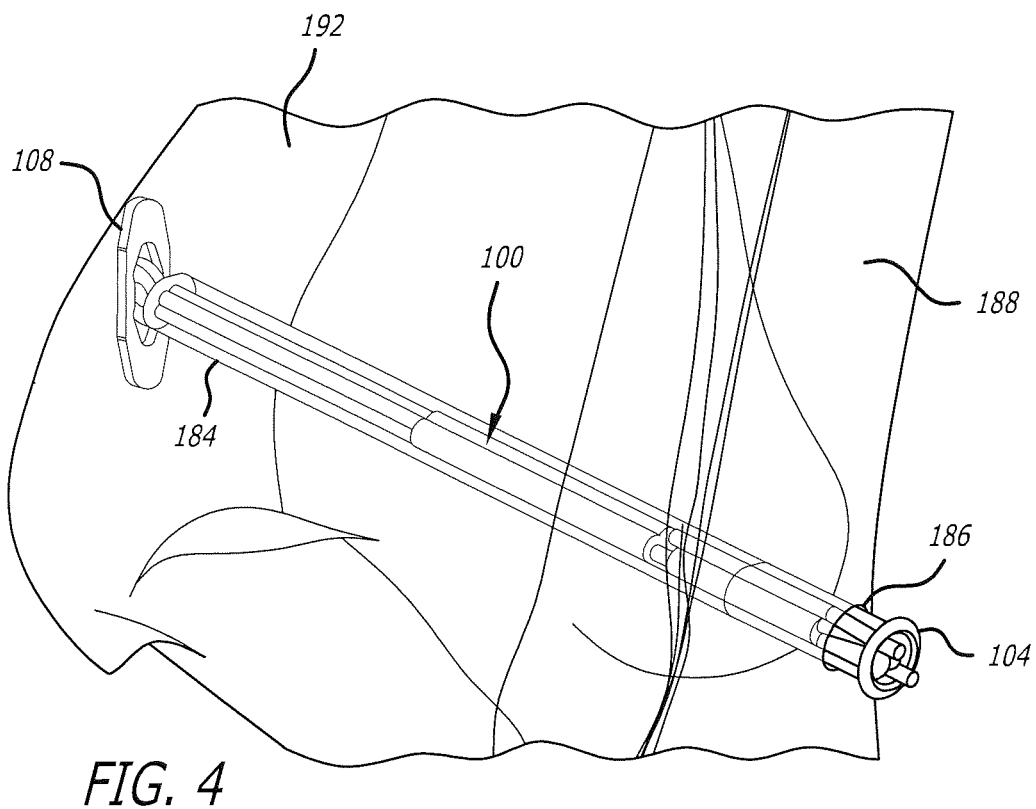
FIG. 4
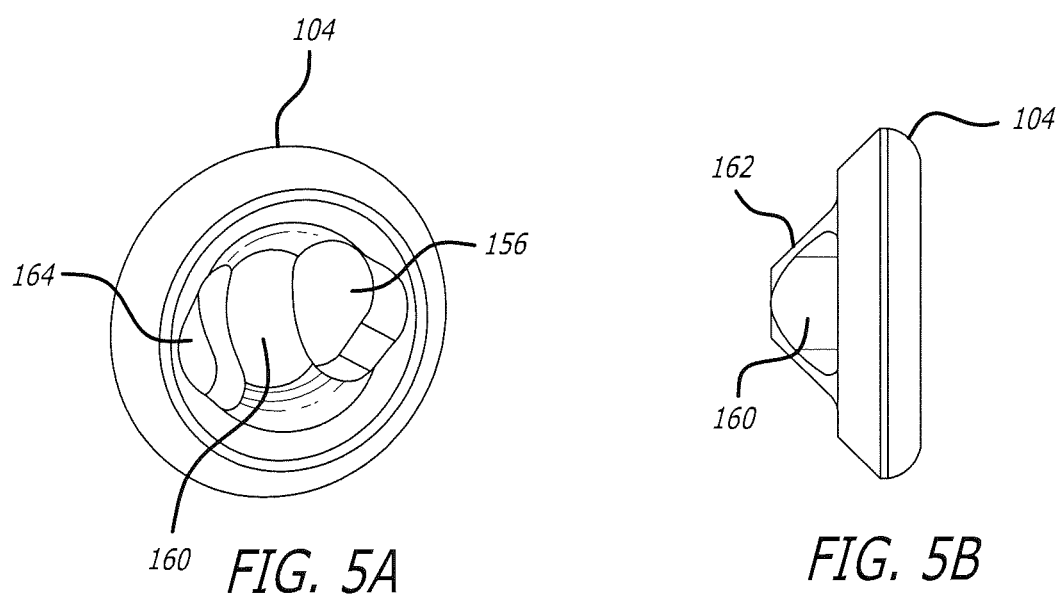
FIG. 5A
FIG. 5B

SYNDESMOSIS TREATMENT CONSTRUCT

FIELD

Embodiments of the present disclosure generally relate to the field of securing bones together. More specifically, embodiments of the disclosure relate to systems and methods for a syndesmosis treatment construct configured to be placed into a cinched configuration that secures a first bone against a second bone.

BACKGROUND

A syndesmosis is a slightly movable fibrous joint in which bones such as the tibia and fibula are joined together by connective tissue. The distal tibia fibular joint and the radioulnar joint are examples of syndesmoses. Injuries to the ankle syndesmosis are common and frequently occur in patients having ankle fractures.

Due to the complex biomechanics of ankle syndesmosis injuries and the relatively increased healing time associated with them, there has been widespread debate on both the strongest and most appropriate methods of fixation when treated operatively. Conventional treatments for ankle syndesmosis injuries include metallic or bioabsorbable screw fixation, as well as various methods of suture button fixation. A benefit of suture button fixation treatments is that they generally do not require additional procedures for removal of implants as do screw fixation treatments.

There is an ongoing need for the development of bone fusion capabilities such as that related to, for example, treating injuries to the ankle syndesmosis. Provided herein are embodiments and methods for a syndesmosis treatment construct configured to be placed into a cinched configuration that presses a first bone against a second bone.

SUMMARY

An apparatus and method are provided for syndesmosis treatment constructs to be passed through a bone hole across a first bone and a second bone and placed into a cinched configuration whereby the first bone and the second bone are pressed together. In one embodiment, the syndesmosis treatment construct comprises a proximal fixator configured to contact the first bone, a distal fixator configured to contact the second bone, and a suture comprising a first segment and a second segment that share an intervening splice. The first segment loops through the distal fixator before passing through the splice and extending from the proximal fixator. The second segment loops through the proximal fixator and passes through the splice before looping through the distal fixator and extending from the proximal fixator. The splice compresses and seizes the first and second segments during pulling ends of the suture by a practitioner, thereby establishing the cinched configuration. In one embodiment, a first suture and a second suture are parallelly looped through the distal fixator. A free splice slidably rides on proximal ends and distal ends of both of the first and second sutures. The distal ends are looped through the proximal fixator and bound within a stitch splice. The proximal ends are passed outside of the stitch splice and through the proximal fixator. The free splices compress and seize the proximal ends during pulling of the proximal ends by a practitioner so as to maintain the cinched configuration.

In an exemplary embodiment, a syndesmosis treatment construct for cinching a first bone and a second bone together comprises: a distal fixator configured to be passed through a bone hole across the first bone and the second bone and contacting the second bone; a proximal fixator configured to contact the first bone; a first suture and a second suture parallelly looped through the proximal fixator and the distal fixator such that a proximal end of the first suture and a proximal end of the second suture extend from the proximal fixator; one or more free splices that slidably ride on adjacent portions of the first suture and the second suture; and one or more stitch splices that fixedly receive distal ends of the first suture and the second suture.

In another exemplary embodiment, the proximal fixator includes a bar that separates a first aperture and a second aperture. In another exemplary embodiment, the distal end of the first suture and the distal end of the second suture loop around the bar before being fixedly received by the one or more stitch splices. In another exemplary embodiment, the proximal end of the first suture passes through the first aperture and the proximal end of the second suture passes through the second aperture.

In another exemplary embodiment, the proximal end of the first suture and the proximal end of the second suture exit the one or more free splices and extend adjacently to the one or more stitch splices toward the proximal fixator. In another exemplary embodiment, the distal end of the first suture and the distal end of the second suture exit the one or more stitch splices, loop around a bar comprising the proximal fixator and are fixedly received into the one or more stitch splices. In another exemplary embodiment, the one or more free splices are configured to compress the portions of the proximal ends within the one or more free splices during tensioning of the first suture and the second suture so as to maintain a cinched configuration of the first bone and the second bone.

In an exemplary embodiment, a syndesmosis treatment construct for cinching a first bone and a second bone together comprises: a distal fixator configured to be passed through a bone hole across the first bone and the second bone and contacting the second bone; a proximal fixator configured to contact the first bone; a suture looped through the proximal fixator and the distal fixator such that opposite suture ends of the suture protrude from the proximal fixator; and a splice comprising a portion of the suture that slidably rides on a first segment of the suture and a second segment of the suture.

In another exemplary embodiment, the splice is configured to compress and seize the first segment and the second segment during pulling the suture ends by a practitioner, thereby cinching the first bone and the second bone together. In another exemplary embodiment, the splice is configured to restrict movement of the first segment and the second segment so as to maintain a cinched configuration of the first bone and the second bone. In another exemplary embodiment, the splice is disposed between the proximal fixator and the distal fixator. In another exemplary embodiment, the splice is configured to be disposed inside the bone hole, the splice having a diameter that is less than a diameter of the bone hole. In another exemplary embodiment, the first segment and the second segment loop through the distal fixator in opposite directions so as to prevent rotation of the distal fixator during cinching of the suture.

In an exemplary embodiment, a method for a syndesmosis treatment construct for cinching a first bone and a second bone together comprises: configuring a distal fixator to be passed through a bone hole across the first bone and the second bone and placed into contact with the second bone; configuring a proximal fixator for contacting the first bone; forming a splice on a suture between a first segment and a second segment; looping the first segment through the distal fixator before passing the first segment through the splice; extending the first segment from the splice through the proximal fixator; looping the second segment through the proximal fixator before passing the second segment through the splice; looping the second segment through the distal fixator; and extending the second segment through the proximal fixator.

In another exemplary embodiment, forming the splice includes configuring the splice to slidably ride on the first segment and the second segment when opposite ends of the suture are pulled by a practitioner. In another exemplary embodiment, forming the splice includes configuring the splice to compress the first segment and the second segment during tensioning of the suture. In another exemplary embodiment, forming the splice further comprises configuring the splice to seize the first segment and the second segment within the splice so as to maintain a cinched configuration of the first bone and the second bone.

In another exemplary embodiment, configuring the proximal fixator includes forming a bar that separates a first aperture and a second aperture. In another exemplary embodiment, looping the second segment includes looping the second segment around the bar before passing the second segment through the splice. In another exemplary embodiment, configuring the distal fixator includes forming a bar that separates a first aperture and a second aperture. In another exemplary embodiment, looping the first segment through the distal fixator includes routing the first segment around the bar in opposition to the second segment.

BRIEF DESCRIPTION OF THE DRAWINGS

The drawings refer to embodiments of the present disclosure in which:

FIG. 4 illustrates an exemplary use environment wherein an exemplary embodiment of a syndesmosis treatment construct is disposed within a bone hole and pressing a first bone and a second bone together, in accordance with the present disclosure;

FIG. 5A illustrates an isometric view of a proximal fixator in accordance with the present disclosure FIG. 5B illustrates a side plan view of the proximal fixator of FIG. 5A, according to the present disclosure;

Figure 1:
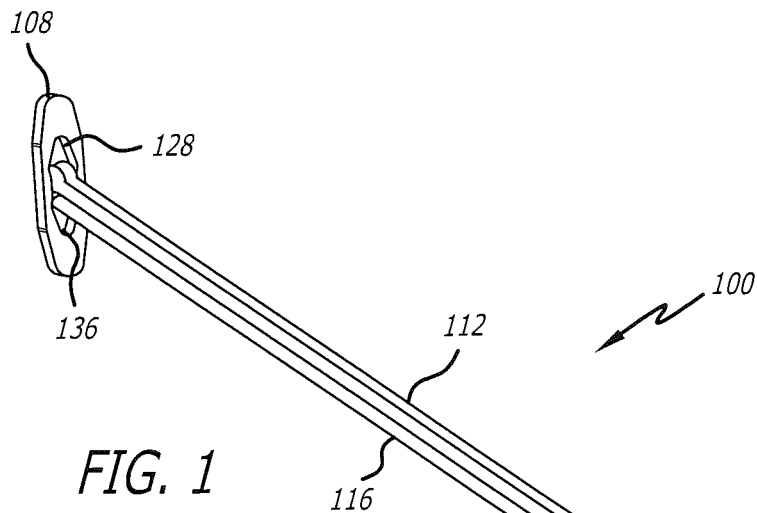
FIG. 1 illustrates an isometric view of an exemplary embodiment of a syndesmosis treatment construct, in accordance with the present disclosure.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

In the following description, numerous specific details are set forth in order to provide a thorough understanding of the present disclosure. It will be apparent, however, to one of ordinary skill in the art that the invention disclosed herein may be practiced without these specific details. In other instances, specific numeric references such as "first suture," may be made. However, the specific numeric reference should not be interpreted as a literal sequential order but rather interpreted that the "first suture" is different than a "second suture." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

A syndesmosis is a slightly movable fibrous joint in which bones such as the tibia and fibula are joined together by connective tissue. The distal tibia fibular joint and the radioulnar joint are examples of syndesmoses. Injuries to the ankle syndesmosis are common and frequently occur in patients having ankle fractures. There is an ongoing need for the development of bone fusion capabilities such as that found in, for example, treating injuries to the ankle syndesmosis. Provided herein are embodiments and methods for a syndesmosis treatment construct configured to be placed into a cinched configuration that presses a first bone against a second bone.

FIG. 1 illustrates an isometric view of an exemplary embodiment of a syndesmosis treatment construct 100, in accordance with the present disclosure. Embodiments of the syndesmosis treatment construct are configured to be passed through a bone hole drilled across a first bone and a second bone and placed into a cinched configuration that presses the first bone and the second bone together. In the embodiment illustrated in FIG. 1, the syndesmosis treatment construct 100 comprises a proximal fixator 104 that is configured to contact the first bone, and a distal fixator 108 that is configured to contact the second bone. As shown, the proximal fixator 104 is generally a round, button-shaped member suitable for contacting bone, and the distal fixator 108 is an oblong-shaped member suitable for contacting bone. As will be appreciated, the oblong-shape of the distal fixator 108 facilitates passing, or drawing, the distal fixator 108 through a bone hole drilled in the bones to be treated. It is contemplated, however, that the proximal and distal fixators 104, 108 may include any of various shapes that are found to be advantageous for pressing bones together, without limitation.

With reference to FIG. 1, a first suture 112 and a second suture 116 are parallelly looped through the proximal fixator 104 and the distal fixator 108 such that a proximal end 120 of the first suture 112 and a proximal end 124 of the second suture 116 extend from the proximal fixator 104. The proximal ends 120, 124 extending from the proximal fixator 104 facilitate a practitioner, such as a surgeon, pulling on the first and second sutures 112, 116 to place the syndesmosis treatment construct 100 into the cinched configuration. As will be appreciated, the first and second sutures 112, 116 are generally comprised of any of various suture materials that are suitable for syndesmosis treatment.

Figure 2:
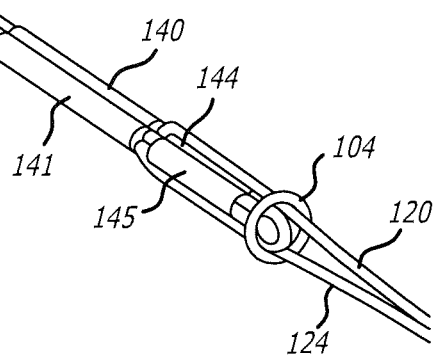
FIG. 2 illustrates an isometric view of a distal portion of the syndesmosis treatment construct shown in FIG. 1.
Figure 2:
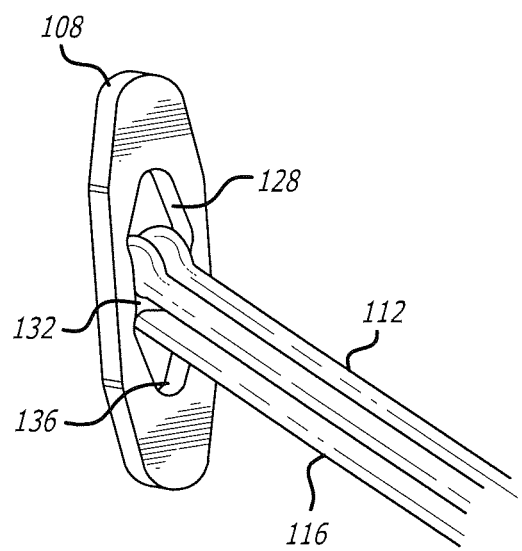

With reference now to FIG. 2, although the first suture 112 and the second suture 116 are parallelly looped through the proximal and distal fixators 104, 108, as disclosed hereinabove, the first and second sutures 112, 116 are looped in opposite directions. More specifically, in the illustrated embodiment, the first suture 112 extends distally through a first aperture 128 comprising the distal fixator 108. The first suture 112 loops around a bar 132 and extends proximally through a second aperture 136 of the distal fixator 108. The second suture 116 extends distally through the second aperture 136, loops around the bar 132 and then extends proximally through the first aperture 128. It is contemplated that looping the first and second sutures 112, 116 in opposite directions serves to inhibit an undesirable rotation of the distal fixator 108 upon cinching the syndesmosis treatment construct 100, as desired herein.

Figure 3A:
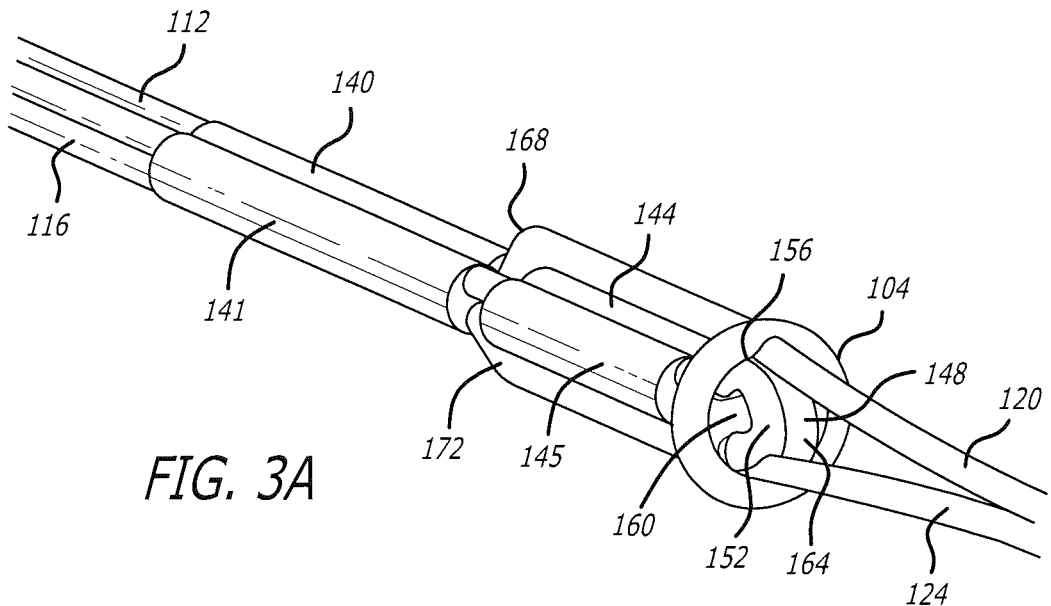
FIG. 3A illustrates an isometric view of a proximal portion of the syndesmosis treatment construct of FIG. 1.

Turning now to FIG. 3A, in the illustrated embodiment, a proximal portion of the syndesmosis treatment construct 100 includes free splices 140, 141 and stitch splices 144, 145. In general, the free splices 140, 141 and the stitch splices 144, 145 cooperate to cinch the syndesmosis treatment construct 100 when the practitioner pulls the proximal ends 120, 124. Further, the free splices 140, 141 and the stitch splices 144, 145 cooperate to maintain the cinched configuration once the practitioner releases the proximal ends 120, 124. It should be understood that since the free splices 140, 141 and the stitch splices 144, 145 are configured to be disposed inside the bone hole, the free splices 140, 141 and the stitch splices 144, 145 preferably have diameters that are less than the diameter of the bone hole.

The free splice 140 comprises a portion of the first suture 112 that slidably rides on an adjacent portion of the first suture 112. In the embodiment of FIG. 3A, the proximal end 120 of the first suture 112 is inserted into, and extends slidably through, a portion of a distal end 148 of the first suture 112. Similarly, the free splice 141 comprises the proximal end 124 of the second suture 116 extending through an interior of a portion of a distal end 152 of the second suture 116. Thus, during pulling by a practitioner, the proximal ends 120, 124 slide within respective free splices 140, 141 as the syndesmosis treatment construct 100 becomes increasingly cinched. As the syndesmosis treatment construct 100 approaches the cinched configuration, tension within the first and second sutures 112, 116 increasingly compresses the portions of the proximal ends 120, 124 within the free splices 140, 141, causing the cinched configuration of the construct 100 to be maintained without the practitioner having to form any surgical knots.

Proximal of the free splices 140, 141, the distal ends 148, 152 loop through the proximal fixator 104 and then are fixedly bound within the stitch splices 144, 145. More particularly, the distal end 152 extends proximally through a first aperture 156 comprising the proximal fixator 104, loops around a bar 160 and then extends distally through a second aperture 164 of the proximal fixator 104 before terminating in the stitch splice 145. As will be appreciated, therefore, the stitch splice 145 essentially comprises a fixation of the distal end 152 to a portion of the distal end 152 that is adjacent to the proximal fixator 104. The distal end 148 extends proximally through the second aperture 164, loops around the bar 160 and extends distally through the first aperture 156 and terminates in the stitch splice 144. Similar to the stitch splice 145, the stitch splice 148 comprises a fixation of the distal end 148 to a portion of the distal end 148 that is adjacent to the proximal fixator 104. The stitch splices 144, 145 generally are disposed near the proximal fixator 104, such that the distal ends 148, 152 are formed into eyelets around the bar 160.

Unlike the distal ends 148, 152, the proximal ends 120, 124 exit the free splices 140, 141 and bypass the stitch splices 144, 145. The proximal end 120 passes through the first aperture 156, and the proximal end 124 passes through the second aperture 164. As stated hereinabove, once the distal fixator 108 has been passed through a bone hole, the practitioner may cinch the syndesmosis treatment construct 100 by pulling on the proximal ends 120, 124 so as to effectively shorten the loops of the first and second sutures 112, 116 between the proximal and distal fixators 104, 108. As will be appreciated, therefore, pulling on the proximal ends 120, 124 causes the proximal and distal fixators 104, 108 to move toward one another until the proximal fixator 104 contacts the first bone and the distal fixator 108 contacts the second bone. Further pulling of the proximal ends 120, 124 places the syndesmosis treatment construct 100 into a cinched configuration that presses the first bone and the second bone together. As described hereinabove, tension within the first and second sutures 112, 116 compresses the portions of the proximal ends 120, 124 within the free splices 140, 141, causing the cinched configuration of the construct 100 to be maintained without the practitioner having to form any surgical knots.

Figure 3B:
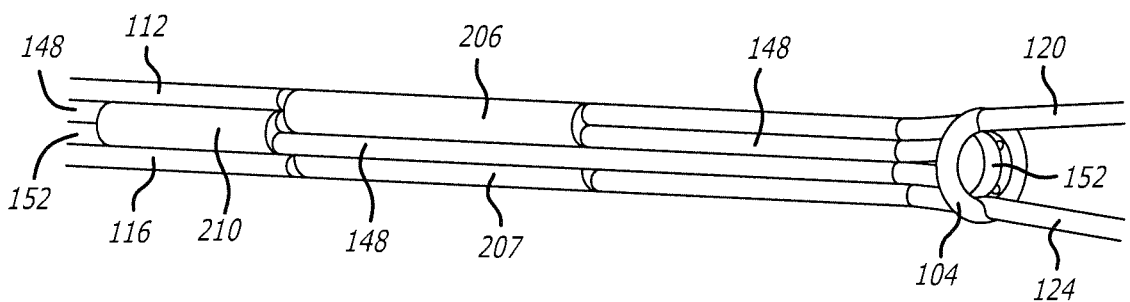
FIG. 3B illustrates an exemplary embodiment of a proximal portion of a syndesmosis treatment construct, in accordance with the present disclosure.

It is to be understood that the syndesmosis treatment construct 100 is not to be limited to the arrangement of free splices 140, 141 and stitch splices 144, 145 shown in, and discussed with reference to, FIG. 3A. For example, in an embodiment illustrated in FIG. 3B, a syndesmosis treatment construct includes a proximal portion 202 wherein a first free splice 206 and a second free splice 207 are proximal of a combined stitch splice 210. The free splices 206, 207 are substantially identical to the free splices 140, 141, with the exception that the free splices 206, 207 are disposed proximal of the stitch splice 210. Similar to the stitch splices 144, 145, the stitch splice 210 comprises portions of the distal ends 148, 152 that are fixated together distal of the free splices 206, 207, respectively. Unlike the stitch splices 144, 145, however, the stitch splice 210 serves as a single stitch splice for both distal ends 148, 152. As will be appreciated, in some embodiments, multiple stitch splices may be implemented in lieu of the stitch splice 210. It is to be understood, therefore, that the syndesmosis treatment construct disclosed herein may be comprised of any combination and any number of free splices and stitch splices that are capable of maintaining the cinched configuration without requiring the practitioner to form any surgical knots, as described herein.

Figure 3C:
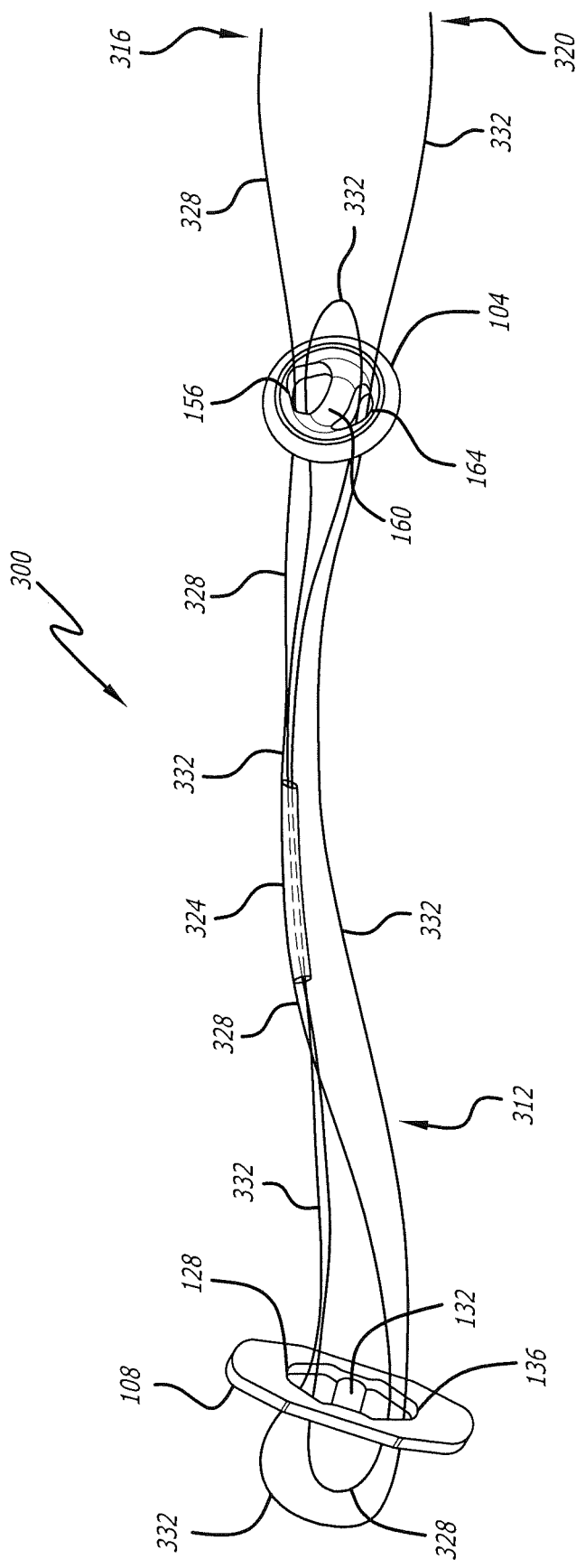
FIG. 3C illustrates a perspective view of an exemplary embodiment of a single-strand syndesmosis treatment construct, in accordance with the present disclosure.

FIG. 3C illustrates a perspective view of an exemplary embodiment of a single-strand syndesmosis treatment construct 300, in accordance with the present disclosure. Embodiments of the single-strand syndesmosis treatment construct 300 are configured to be passed through a bone hole drilled across a first bone and a second bone and placed into a cinched configuration that presses the first bone and the second bone together. In the embodiment illustrated in FIG. 3C, the syndesmosis treatment construct 300 comprises a proximal fixator 104 that is configured to contact the first bone, and a distal fixator 108 that is configured to contact the second bone. As shown, the proximal fixator 104 is generally a round, button-shaped member suitable for contacting bone, and the distal fixator 108 is an oblong-shaped member suitable for contacting bone. As will be appreciated, the oblong-shape of the distal fixator 108 facilitates passing, or drawing, the distal fixator 108 through a bone hole drilled in the bones to be treated. It is contemplated, however, that the proximal and distal fixators 104, 108 may include any of various shapes that are found to be advantageous for pressing bones together, without limitation.

With continuing reference to FIG. 3C, a single strand of suture 312 is looped through the proximal fixator 104 and the distal fixator 108 such that opposite suture ends 316, 320 extend from the proximal fixator 104. The suture 312 includes a splice 324 disposed between a first segment 328 and a second segment 332 of the suture 312. The splice 324 is configured to slidably ride on portions of the first and second segments 328, 332 extending between the proximal and distal fixators 104, 108. The opposite suture ends 316, 320 extending from the proximal fixator 104 facilitate a practitioner, such as a surgeon, pulling on the first and second segments 328, 332 to place the syndesmosis treatment construct 300 into the cinched configuration. As will be appreciated, the suture 312 generally may be comprised of any of various suture materials that are suitable for syndesmosis treatment. Further, it should be understood that since the splice 324 is to be drawn inside the bone hole, a diameter of the splice 324 preferably is less than the diameter of the bone hole.

As will be recognized, the first and second segments 328, 332 are parallelly looped through the distal fixator 108, but the first and second segments 328, 332 are looped in opposite directions. In the illustrated embodiment, for example, the second segment 332 extends distally through a first aperture 128 of the distal fixator 108, loops around a bar 132 and extends proximally through a second aperture 136 of the distal fixator 108. The first segment 328 extends distally through the second aperture 136, loops around the bar 132 and then extends proximally through the first aperture 128. It is contemplated that looping the first and second segments 328, 332 in opposite directions serves to inhibit an undesirable rotation of the distal fixator 108 upon cinching the syndesmosis treatment construct 300, as described herein.

With continuing reference to FIG. 1, the splice 324 generally is configured to maintain the cinched configuration of the syndesmosis treatment construct 300 when the practitioner pulls the suture ends 316, 320, as mentioned above. While the suture ends 316, 320 are being pulled, the splice 324 slidably rides on the first and second segments 328, 332 as the proximal and distal fixators 104, 108 are drawn closer together. Once the proximal fixator 104 contacts the first bone and the distal fixator 108 contacts the second bone, further pulling of the suture ends 316, 320 places the syndesmosis treatment construct 300 into the cinched configuration whereby the first bone and the second bone are pressed together. As the syndesmosis treatment construct 300 cinches, however, tension within the suture 312 causes the splice 324 to increasingly compress and restrict movement of the first and second segments 328, 332, thereby maintaining the cinched configuration. It is contemplated that the practitioner may further secure the cinched configuration of the syndesmosis treatment construct 300 by manipulating the suture ends 316, 320 into any of various surgical knots.

As described hereinabove, the splice 324 comprises a portion of the suture 312 that is disposed between the first segment 328 and the second segment 332. As such, it should be understood that the first and second segments 328, 332 are fixed to opposite sides of the splice 324 with the first segment 328 extending distally from the splice 324 and the second segment 332 extending proximally from the splice 324. The first segment 328, after looping through the distal fixator 108 as described above, passes through the splice 324 and then extends through a first aperture 156 of the proximal fixator 104. The portion of the first segment 328 extending through the first aperture 156 comprises the suture end 316. The second segment 332 extends proximally through the first aperture 156 of the proximal fixator 104, loops around a bar 160 and extends distally through a second aperture 164 of the proximal fixator 104. The second segment 332 passes distally through the splice 324 before extending through the first aperture 128 of the distal fixator 108, as described hereinabove. The second segment 332 loops around the bar 132 and extends through the second aperture 136. The second segment 332 then extends proximally from the distal fixator 108 through the second aperture 164 of the proximal fixator 104. The portion of the second segment 332 protruding from the second aperture 164 comprises the suture end 320.

Methods for configuring the single-strand syndesmosis treatment construct 300 for being passed through a bone hole across a first bone and a second bone and placed into a cinched configuration whereby the first bone and the second bone are pressed together include, in some embodiments, configuring a proximal fixator 104 for contacting the first bone and configuring a distal fixator 108 for contacting the second bone. The methods include, in some embodiments, forming a splice 324 on a suture 312 between a first segment 328 and a second segment 332 of the suture 312. In some embodiments, the methods include looping the first segment 328 through the distal fixator 108 before passing the first segment 328 through the splice 324 and then extending the first segment 328 from the splice 324 through the proximal fixator 104. In some embodiments, the methods include looping the second segment 332 through the proximal fixator 104 before passing the second segment 332 through the splice 324 and then looping the second segment 332 through the distal fixator 108 before extending the second segment 332 through the proximal fixator 104.

The methods can further include, in some embodiments, configuring the splice 324 to slidably ride on the first segment 328 and the second segment 332 when opposite ends 316, 320 of the suture 312 are pulled by a practitioner. In some embodiments, the methods may include configuring the splice 324 to compress the first segment 328 and the second segment 332 during tensioning of the suture 312. The methods can further include, in some embodiments, configuring the splice 324 to seize the first segment 328 and the second segment 332 within the splice 324 so as to maintain the cinched configuration.

FIG. 4 illustrates an exemplary use environment wherein an exemplary embodiment of a syndesmosis treatment construct 100 is disposed within a bone hole 184 and pressing a first bone 188 and a second bone 192 together, in accordance with the present disclosure. The syndesmosis treatment construct 100 comprises a proximal fixator 104 that is configured to contact the first bone 184, and a distal fixator 108 that is configured to contact the second bone 192. In the embodiment illustrated in FIG. 4, the proximal fixator 104 is seated within a proximal opening 186 of the bone hole 184. In some embodiments, however, a bone fusion plate may be implemented to provide support for the proximal fixator 104, as desired. Further, in some embodiments, the single-strand syndesmosis treatment construct 300 of FIG. 3C may be implemented to press the first and second bones 188, 192 together, in lieu of the syndesmosis treatment construct 100.

FIGS. 5A-5B respectively illustrate an isometric view and a side plan view of the proximal fixator 104 in accordance with the present disclosure. The proximal fixator 104 generally is a cone-shaped member configured to seat within the proximal opening 186 of the bone hole 184 as shown in FIG. 4. As shown in FIGS. 5A-5B, the proximal fixator 104 includes a first aperture 156 and a second aperture 164 that are oppositely disposed on the proximal fixator and are separated by a bridge, or fin 160. As best shown in FIG. 5B, the fin 160 includes a cone-shaped profile 162 that is configured to center the proximal fixation 104 within the proximal opening 186 of the bone hole 184. As discussed herein, the apertures 156, 164 are configured to contribute to maintaining the cinched configuration of the syndesmosis treatment construct 100.

Figure 7A:
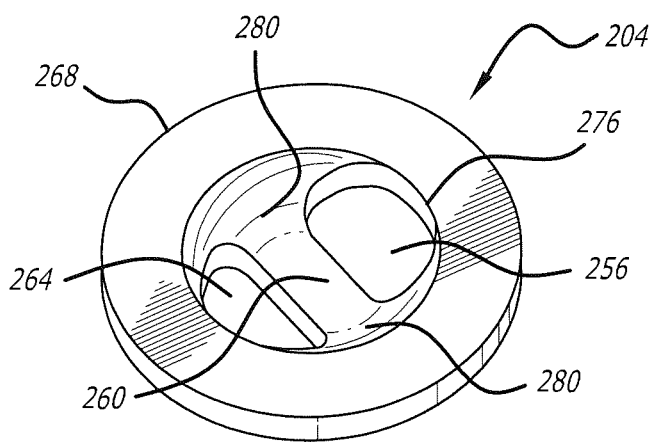
FIG. 7A illustrates an upper perspective view of an exemplary embodiment of a proximal fixator in accordance with the present disclosure
Figure 7B:
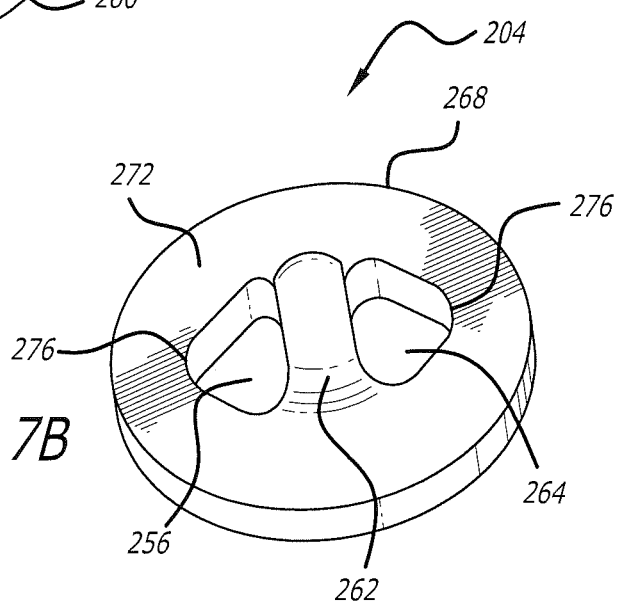
FIG. 7B illustrates a lower perspective view of the proximal fixator of FIG. 7A, according to the present disclosure.

FIGS. 7A-7B respectively illustrate upper and lower perspective views of an exemplary embodiment of a proximal fixator 204 according to the present disclosure. Similar to the proximal fixator 104 shown in FIGS. 5A-5B, the proximal fixator 204 generally is configured to seat within the proximal opening 186 of the bone hole 184 as shown in FIG. 4. As shown in FIGS. 7A-7B, the proximal fixator 204 includes a first aperture 256 and a second aperture 264 that are separated by a fin, or saddle 260. As best shown in FIG. 7B, the saddle 260 includes a cone-shaped profile 262 that operates to center the proximal fixator 204 within the opening 186 of the bone hole 184. Similar to the apertures 156, 164, the first and second apertures 256, 264 cooperatively contribute to maintaining the cinched configuration of the syndesmosis treatment construct 100.

It should be understood that the proximal fixator 204 is configured to seat within the proximal opening 186 of the bone hole 184, as well as contact the bone surface surrounding the opening 186 in absence of a bone fusion plate or other plating system. As such, the proximal fixator 204 includes a periphery 268 having a diameter that is generally larger than the periphery of the proximal fixator 104. In an embodiment, the diameter of the periphery 268 is substantially 6 millimeters (mm). In some embodiments, the diameter of the periphery 268 ranges between substantially 5.2 mm and substantially 6.2 mm, without limitation. Further, the proximal fixator 204 includes a flat undersurface 272 that is configured to advantageously contact the bone surface surrounding the opening 186.

As will be appreciated, the larger diameter of the proximal fixator 204 affords relatively larger apertures 256, 264 than are incorporated into smaller diameter fixators. For example, each of the first and second apertures 256, 264 include peripheral curved portions 276 having a relatively larger radius than smaller diameter fixators. It is contemplated that the peripheral curved portions 276 advantageously prevent damage to the first and second sutures 112, 116 that may otherwise occur due to smaller curved portions. Moreover, the saddle 260 includes curved portions 280 having relatively large radii to prevent potential damage to the distal ends 148, 152 of the sutures 112, 116.

Figure 6A:
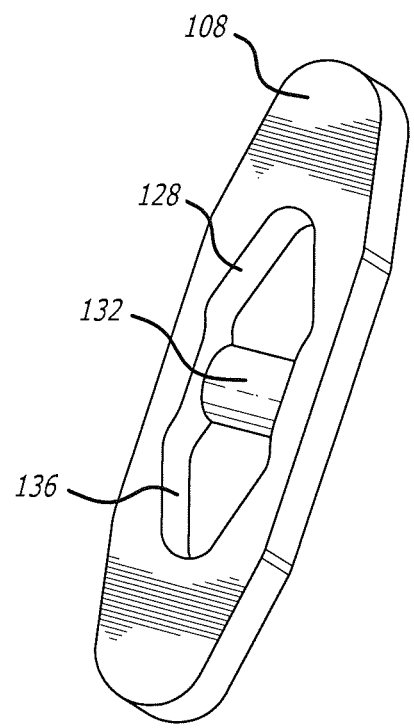
FIG. 6A illustrates a close-up isometric view of a distal fixator, according to the present disclosure.
Figure 6B:
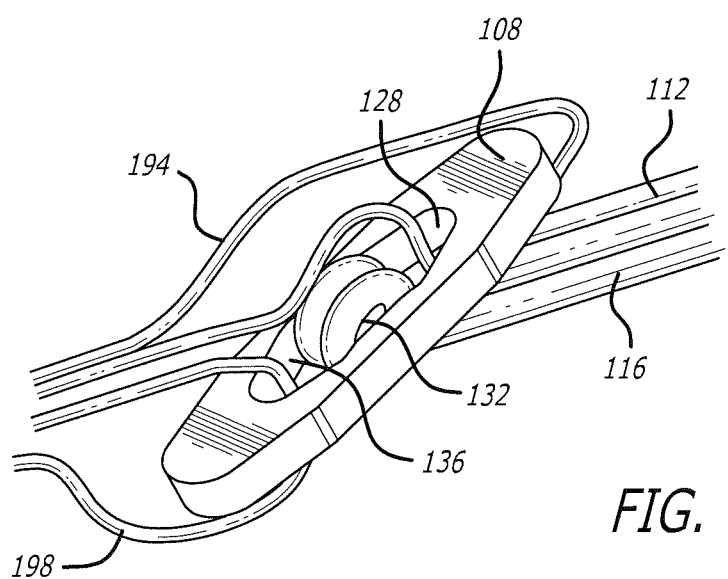
FIG. 6B illustrates an exemplary routing of a first suture loop and a second suture loop through the apertures of a distal portion of the syndesmosis treatment construct of FIG. 1 in preparation for being drawn through a bone hole, according to the present disclosure.

Turning now to FIGS. 6A-6B, the distal fixator 108 is a generally oblong-shaped member suitable for contacting bone. In the embodiment illustrated in FIGS. 6A-6B, the distal fixator 108 includes a first aperture 128 and a second aperture 136 that are separated by a bar 132. As will be appreciated, the oblong-shape of the distal fixator 108 facilitates pulling the distal fixator through the bone hole 184 before the first and second bones 188, 192 are cinched together. For example, in one embodiment shown in FIG. 6B, a first suture 194 is extended from a distal opening of the bone hole 184 and looped through the first aperture 128 while a second suture 198 is extended from the distal opening of the bone hole 184 and looped through the second aperture 136. In the configuration shown in FIG. 6B, either of the first and second sutures 194, 198 may be pulled distally to align a longitudinal aspect of the distal fixator 108 with the bone hole 184 and draw the distal fixator 108 therethrough. Once the distal fixator 108 exits the distal opening of the bone hole 184, the first and second sutures 194, 198 may be used to cause the distal fixator 108 to lay flat against the distal bone surface during cinching of the syndesmosis treatment construct 100.

Figure 8:
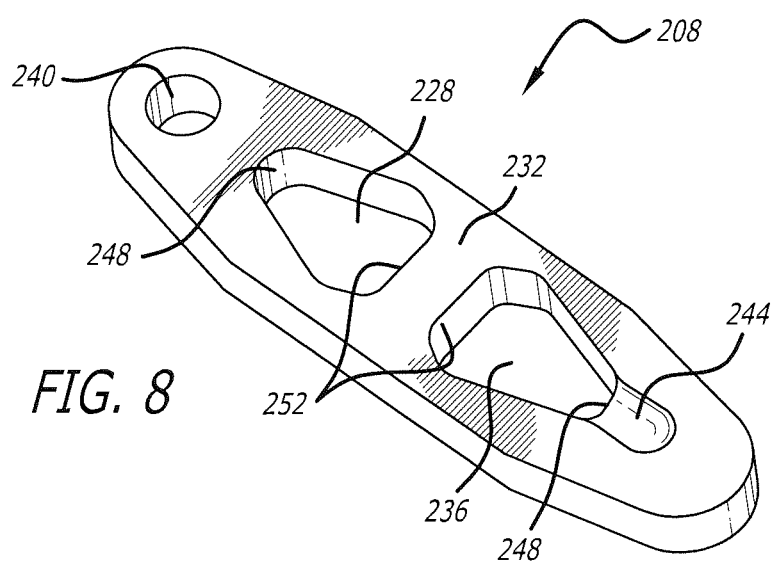
FIG. 8 illustrates a perspective view of an exemplary embodiment of a distal fixator, according to the present disclosure.

FIG. 8 illustrates a perspective view of an exemplary embodiment of a distal fixator 208, according to the present disclosure. Similar to the distal fixator 108 of FIGS. 6A-6B, the distal fixator 208 is a generally oblong-shaped member configured to contact bone. The distal fixator 208 includes a first aperture 228 and a second aperture 236 that are separated by a saddle 232. As discussed herein, the oblong-shape of the distal fixator 208 enables the distal fixator to be drawn through the bone hole 184 before the first and second bones 188, 192 are cinched together.

In the embodiment shown in FIG. 8, the distal fixator 208 includes a deployment suture hole 240 and a suture cradle 244 disposed at opposite ends of the distal fixator. As will be appreciated, the deployment suture hole 240 facilitates pulling the distal fixator 208 through the bone hole 184. For example, the suture 198 shown in FIG. 6B may be extended from a distal opening of the bone hole 184 and looped through the deployment suture hole 240 and then pulled to align a longitudinal aspect of the distal fixator 208 with the bone hole 184. The suture 198 may be further pulled to draw the distal fixator 208 all the way through the bone hole 184. The suture cradle 244 provides a smooth, curved valley that operates to protect the sutures 112, 116 while the distal fixator 208 is drawn through the bone hole 184. Once the distal fixator 208 exits the distal opening of the bone hole 184, the distal fixator may be laid flat against the distal bone surface during cinching of the syndesmosis treatment construct 100.

In general, the embodiment of the distal fixator 208 illustrated in FIG. 8 is relatively thicker and stronger than the distal fixator 108, shown in FIG. 6A-6B. Further, each of the first and second apertures 228, 236 includes peripheral curved portions 248 having relatively larger radii than the apertures 128, 136. Furthermore, the saddle 232 includes curved portions 252 having greater radii that the curved portions incorporated into the bar 132. As will be appreciated, the curved portions 252, as well as the peripheral curved portions 248, advantageously prevent damage to the sutures 112, 116 that might otherwise occur during drawing the proximal fixator 208 through the bone hole 184 and during cinching the syndesmosis treatment construct 100.

Methods for configuring the syndesmosis treatment construct 100 for being passed through a bone hole and placed into a cinched configuration whereby a first bone and a second bone are pressed together include, in some embodiments, looping a first suture 112 and a second suture 116 parallelly through a distal fixator 108, and configuring free splices 140, 141 to slidably ride on proximal ends 120, 124 of the first suture 112 and the second suture 116. The methods include, in some embodiments, looping the distal end 148 of the first suture 112 and the distal end 152 of the second suture 116 around a bar 160 comprising a proximal fixator 104. In some embodiments, the bar separates a first aperture 156 and a second aperture 164.

The methods can further include, in some embodiments, configuring stitch splices 144, 145 to fixate each of the distal end 148 of the first suture 112 and the distal end 152 of the second suture 116 so as to retain the bar 160 within a first eyelet comprising the first suture 112 and a second eyelet comprising the second suture 116. In some embodiments, the methods include configuring the free splices 140, 141 to compress and seize the portions of the proximal ends 120, 124 within the free splices during tensioning of the first and second sutures 112, 116 so as to maintain the cinched configuration.

The methods can further include, in some embodiments, passing the proximal end 120 of the first suture 112 outside the stitch splice 144 and through the first aperture 156. In some embodiments, the methods include passing the proximal end 124 of the second suture 116 outside the stitch splice 145 and through the second aperture 164. In some embodiments, the methods can further include configuring the free splices 140, 141 to compress and seize the portions of the proximal ends 120, 124 within the free splices 140, 141 during pulling of the proximal ends 120, 124 by a practitioner so as to maintain the cinched configuration.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. A syndesmosis treatment construct for cinching a first bone and a second bone together, the syndesmosis treatment construct comprising:
   a distal fixator configured to be passed through a bone hole across the first bone and the second bone and contacting the second bone;
   a proximal fixator configured to contact the first bone;
   a suture looped through the proximal fixator and the distal fixator such that opposite suture ends of the suture protrude from the proximal fixator;
   a splice comprising a portion of the suture that slidably rides on a first segment of the suture and a second segment of the suture; and wherein the first segment and the second segment loop through the distal fixator in opposite directions so as to prevent rotation of the distal fixator during cinching of the suture.

2. The syndesmosis treatment construct of claim 1, wherein the splice is configured to compress and seize the first segment and the second segment during pulling the suture ends by a practitioner, thereby cinching the first bone and the second bone together.

3. The syndesmosis treatment construct of claim 2, wherein the splice is configured to restrict movement of the first segment and the second segment so as to maintain a cinched configuration of the first bone and the second bone.

4. The syndesmosis treatment construct of claim 1, wherein the splice is disposed between the proximal fixator and the distal fixator.

5. The syndesmosis treatment construct of claim 1, wherein the splice is configured to be disposed inside the bone hole, the splice having a diameter that is less than a diameter of the bone hole.

* * * * *